United States Patent
Lynch et al.

(10) Patent No.: US 9,822,064 B2
(45) Date of Patent: Nov. 21, 2017

(54) METHODS OF PRODUCING CANCER TREATING COMPOUNDS

(71) Applicant: Inspyr Therapeutics, Inc., San Antonio, TX (US)

(72) Inventors: John K Lynch, Cedarburg, WI (US); Jeff Hutchison, Sheboygan, WI (US); Xiong Fu, Superior, CO (US); Kevin Kunnen, Plymouth (IN)

(73) Assignee: Inspyr Therapeutics, Inc., Westlake Village, CA (US)

( * ) Notice: Subject to any disclaimer, the term of this patent is extended or adjusted under 35 U.S.C. 154(b) by 0 days.

(21) Appl. No.: 15/232,590

(22) Filed: Aug. 9, 2016

(65) Prior Publication Data

US 2016/0347706 A1   Dec. 1, 2016

Related U.S. Application Data

(62) Division of application No. 14/776,730, filed as application No. PCT/US2014/029674 on Mar. 14, 2014, now Pat. No. 9,446,141.

(60) Provisional application No. 61/791,909, filed on Mar. 15, 2013.

(51) Int. Cl.

| | |
|---|---|
| C07C 227/16 | (2006.01) |
| C07D 307/93 | (2006.01) |
| C07K 5/072 | (2006.01) |
| C07C 269/04 | (2006.01) |
| C07C 269/06 | (2006.01) |
| C07C 227/18 | (2006.01) |
| A61K 31/365 | (2006.01) |
| A61K 47/48 | (2006.01) |
| C07C 227/02 | (2006.01) |
| C07C 229/08 | (2006.01) |
| C07C 271/22 | (2006.01) |

(52) U.S. Cl.
CPC .......... *C07C 227/16* (2013.01); *A61K 31/365* (2013.01); *A61K 47/48246* (2013.01); *C07C 227/02* (2013.01); *C07C 227/18* (2013.01); *C07C 229/08* (2013.01); *C07C 269/04* (2013.01); *C07C 269/06* (2013.01); *C07C 271/22* (2013.01); *C07D 307/93* (2013.01); *C07K 5/06104* (2013.01); *C07K 5/06113* (2013.01)

(58) Field of Classification Search
CPC .................................................. C07C 227/16
See application file for complete search history.

(56) References Cited

U.S. PATENT DOCUMENTS

| | | | |
|---|---|---|---|
| 7,468,354 B2 | 12/2008 | Isaacs | |
| 7,767,648 B2 | 8/2010 | Isaacs | |
| 9,446,141 B2 * | 9/2016 | Lynch | C07D 307/93 |

FOREIGN PATENT DOCUMENTS

| | | |
|---|---|---|
| WO | WO 01/93861 | 12/2001 |
| WO | WO 02/43773 A2 | 6/2002 |
| WO | WO 2010/107909 | 9/2010 |

OTHER PUBLICATIONS

Extended European Search Report dated Oct. 17, 2016.
Shinnosuke Machida et al., "Module Assembly for Protein-Surface Recognition: Geranylgeranyltransferase I Bivalent Inhibitors for Simultaneous Targeting of Interior and Exterior Protein Surfaces", Chemistry, a European Journal, Wiley—V C H Verlag GMBH & Co. KGAA, Weinheim, DE, vol. 14, No. 5, Feb. 8, 2008 (pp. 1392-1401).
Carsten M. Jakobsen et al., "Design, Synthesis, and Pharmacological Evaluation of Thapsigargin Analogues for Targeting Apoptosis to Prostatic Cancer Cells", Journal of Medicinal Chemistry, vol. 44, No. 26, Dec. 2001 (pp. 4696-4703).
Arwin J. Brouwer et al., "Convergent Synthesis and Diversity of Amino Acid Based Dendrimers", European Journal of Organic Chemistry, vol. 2001, No. 10, Apr. 18, 2001 (pp. 1903-1915).
Singapore Search Report dated Sep. 3, 2016.
Singapore Written Opinion dated Sep. 3, 2016.

* cited by examiner

*Primary Examiner* — Golam M M Shameem
(74) *Attorney, Agent, or Firm* — Holly Logue; Elie Gendloff; Lewis Roca Rothgerber Christie LLP

(57) ABSTRACT

Provided herein are methods of making the compound of Formula I:

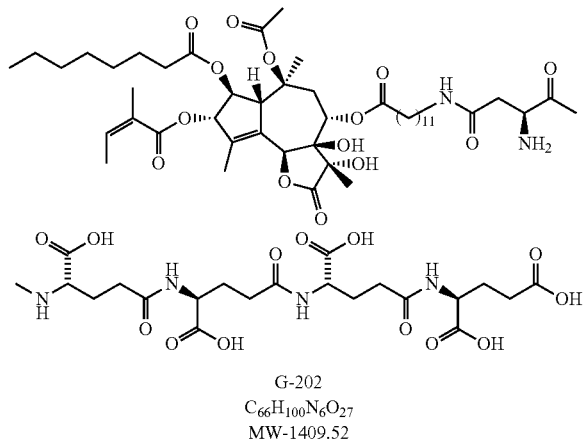

G-202
$C_{66}H_{100}N_6O_{27}$
MW-1409.52 and certain intermediates involved in such process.

9 Claims, 4 Drawing Sheets

Synthesis of G-202

Step 1: Synthesis of Linker

Step 2: Synthesis of DBTg

Step 3: Synthesis of BOC-12-ADT

Step 4: Synthesis of 12-ADT (TFA salt)

Step 5: PG-202

Step 6: Crude G-202 (TFA Salt)

Step 7: Purified G-202 (Free Base)

METHODS OF PRODUCING CANCER TREATING COMPOUNDS

PRIORITY

This application claims priority to U.S. application Ser. No. 14/776,730, filed Mar. 14, 2014, PCT Appln. No. PCT/US14/29674, filed Mar. 14, 2014, and to U.S. Provisional Application No. 61/791,909, filed Mar. 15, 2013, each of which is hereby incorporated by reference in its entirety.

FIELD OF THE INVENTION

The invention relates to methods of making prodrug compounds useful against cancer. In one example, the invention relates to methods of making a prodrug comprising the thapsigargin derivative 8-O-(12-aminododecanoyl)-8-O-debutanoyl thapsigargin (12ADT) linked to the aspartic acid of a peptide having the sequence Asp-Glu*Glu*Glu*Glu, wherein at least one of the bonds designated with * is a gamma carboxy linkage, and having the formula of Formula 1:

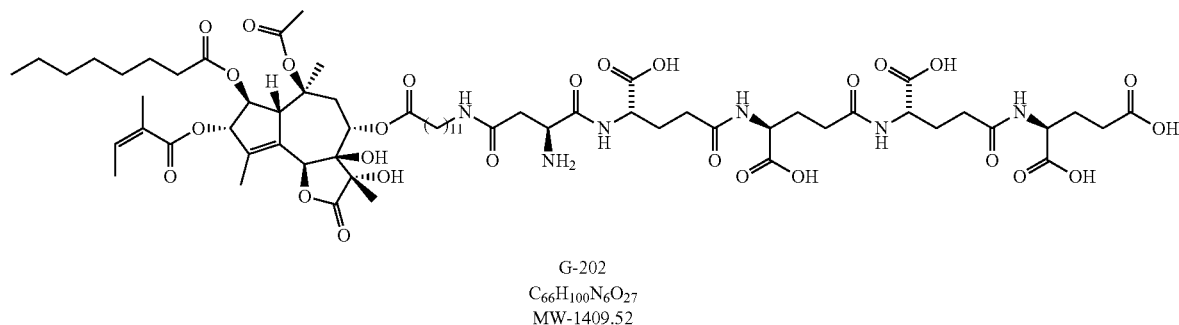

G-202
$C_{66}H_{100}N_6O_{27}$
MW-1409.52 as well as methods of making certain intermediates thereof. The invention also relates to the compounds and intermediates obtained by the processes herein set forth.

BACKGROUND OF THE INVENTION

A peptide prodrug compound identified as G-202, and comprising the thapsigargin derivative 8-O-(12-aminododecanoyl)-8-O-debutanoyl thapsigargin (12ADT) linked to the aspartic acid of a peptide having the sequence Asp-Glu*Glu*Glu*Glu, wherein at least one of the bonds designated with * is a gamma carboxy linkage and having the structural formula:

(Formula 1) has been set forth and described in U.S. Pat. Nos. 7,767,648 and 7,468,354, which are incorporated herein in their entireties. Injectable cancer compositions comprising G-202 and Methods and Compositions for Treating Hepatocellular Carcinoma using G-202 are also disclosed in U.S. Provisional application Ser. Nos. 61/714,662 and, 61/693,273, which are incorporated herein in their entireties.

The major challenge for a process to produce G-202 is due to the lack of crystallinity of any of the intermediates or final active pharmaceutical ingredient (API). This precludes the use of crystallization for removal of impurities at any point in the synthesis. This constraint makes it essential that the reactions be highly efficient and generate little to no impurities. In addition, the lack of crystallinity increases the value of alternate purification processes such as aqueous extractions, polar/non-polar organic partitioning, precipitation, trituration and efficient chromatographic purification. This process disclosed herein successfully incorporates an effective synthetic strategy and all of these purification techniques to generate pure G-202.

SUMMARY OF THE INVENTION

In one aspect, the invention provides a method for making the compound of Formula I:

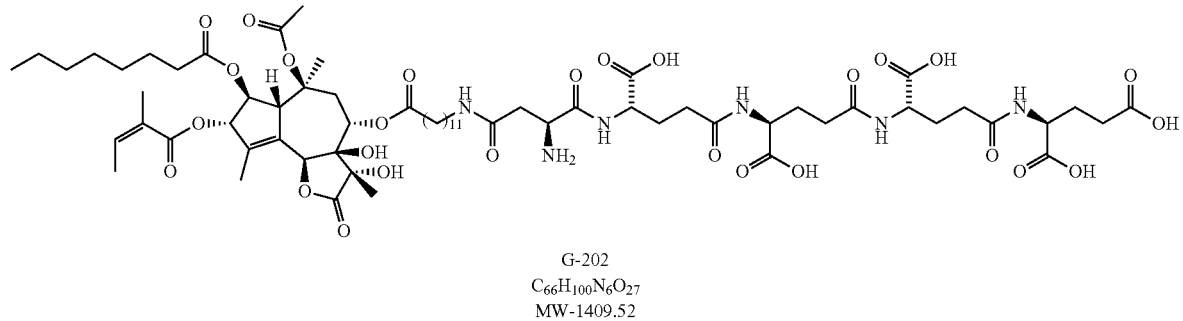

G-202
$C_{66}H_{100}N_6O_{27}$
MW-1409.52

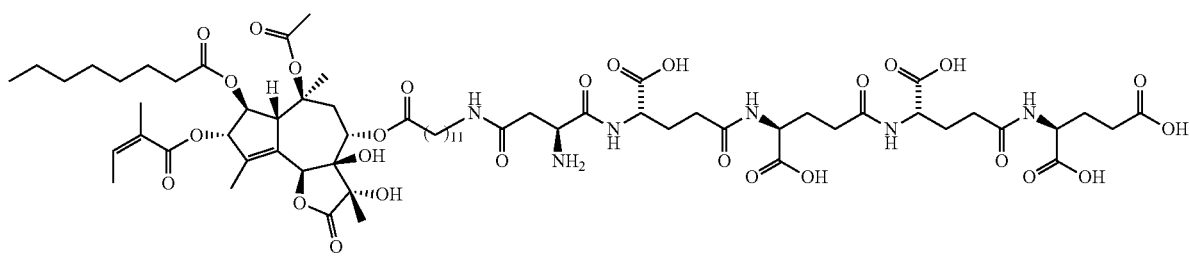

G-202
C$_{66}$H$_{100}$N$_6$O$_{27}$
MW-1409.52 having the chemical name 8-O-(12-aminododecanoyl)-8-O-debutanoyl-thapsigargin) aspartate-γ-glutamate-γ-glutamate-γ-glutamate-glutamate OH, which comprises:

(a) modifying thapsigargin (Tg) (Formula 2)

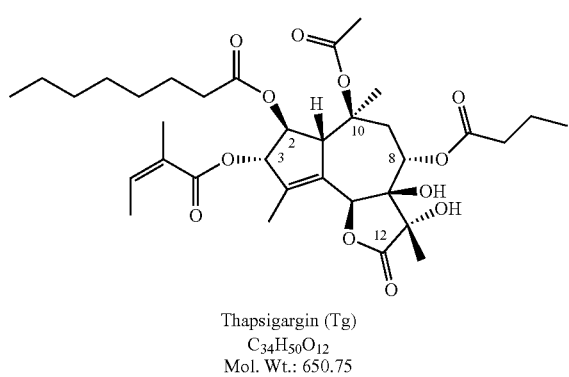 [SMILES: C/C=C(/C)C(=O)O[C@H]1C(C)=C2[C@H]([C@@H]1OC(=O)CCCCCCC)[C@@](C)(OC(C)=O)C[C@H](OC(=O)CCC)[C@@]1(O)[C@H]2OC(=O)[C@@]1(C)O]

Thapsigargin (Tg)
C$_{34}$H$_{50}$O$_{12}$
Mol. Wt.: 650.75 to yield the compound 8-O-Debutanoyl-thapsigargin (DBTg) (Formula 3):

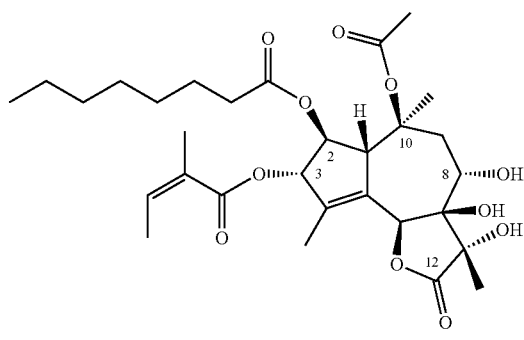

8-O-Debutanoyl-thapsigargin (DBTg)
C$_{30}$H$_{44}$O$_{11}$
Mol. Wt.: 580.66 and (b) adding the compound Boc-12-AD (Formula 4) in the presence of dimethylaminopyridine (DMAP), diisopropylcarbodiimide (DIC) and CH$_2$Cl$_2$:

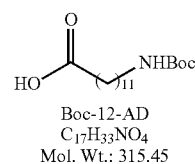

Boc-12-AD
C$_{17}$H$_{33}$NO$_4$
Mol. Wt.: 315.45 to yield Boc-12ADT (Formula 5):

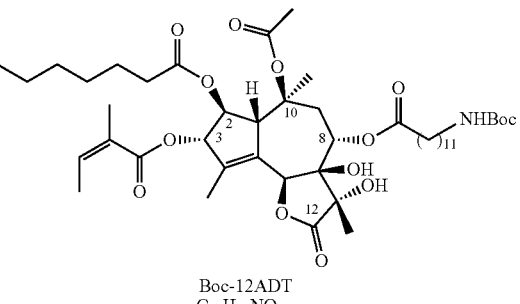

Boc-12ADT
C$_{47}$H$_{75}$NO$_{14}$
Mol. Wt.: 878.1 and (c) deprotecting BOC-12ADT to yield 12-ADT (Formula 6):

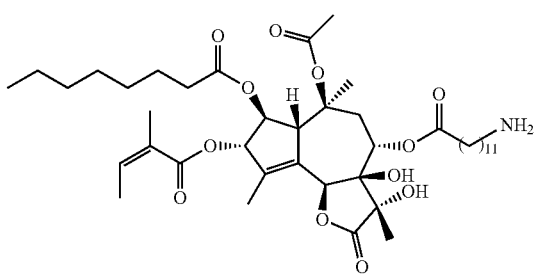

12-ADT
C$_{42}$H$_{67}$NO$_{12}$
Mol. Wt.: 777.98
(TFA salt MW = 892.00)

and (d) combining 12-ADT with Boc-Asp-Glu(OtBu)-Glu(OtBu)-Glu(OtBu)-OtBu (Formula 7):

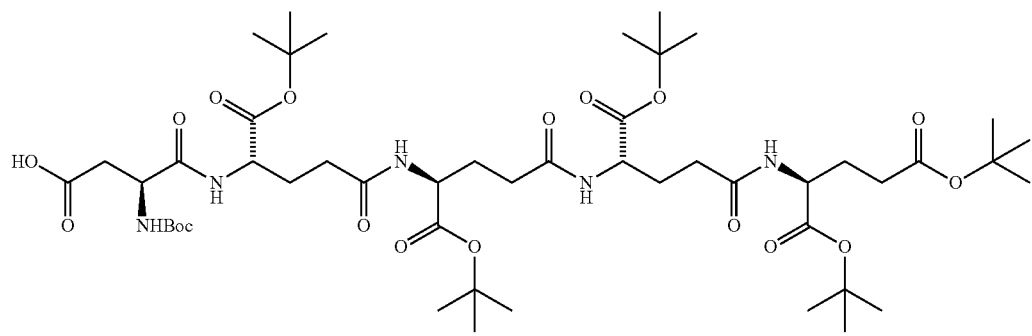

Boc-Asp-Glu(OtBu)-Glu(OtBu)-Glu(OtBu)-OtBu
C₄₉H₈₃N₅O₁₈
Mol. Wt.: 1030.21 in the presence of ethyl-(dimethylaminopropyl)carbodiimide (EDC), diisopropylethylamine (iPr₂NEt), hydroxybenzotriazole (HOBt), and dimethylformamide (DMF) to yield PG-202 (Formula 8):

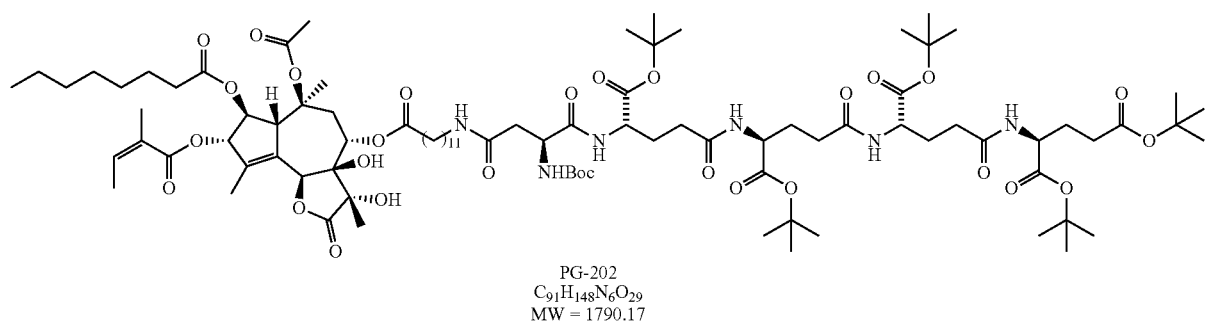

PG-202
C₉₁H₁₄₈N₆O₂₉
MW = 1790.17 and (e) reacting PG-202 to yield the compound Crude G-202 (Formula 9):

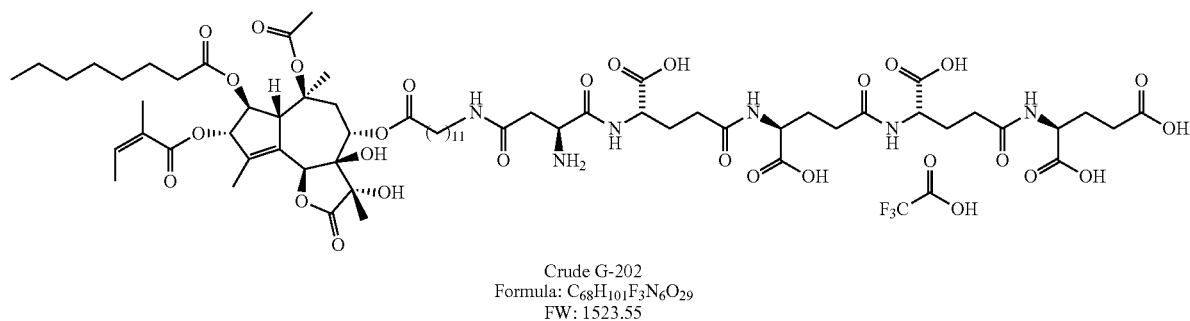

Crude G-202
Formula: C₆₈H₁₀₁F₃N₆O₂₉
FW: 1523.55 and (f) then converting Crude G-202 to the compound of Formula 1.

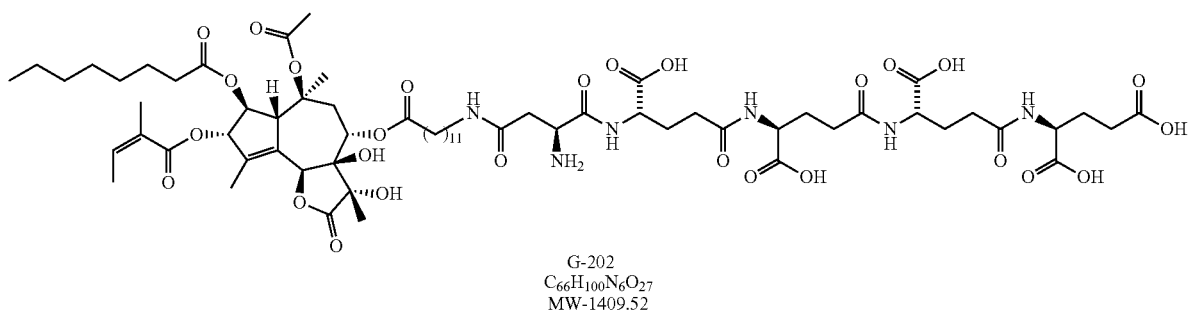

G-202
$C_{66}H_{100}N_6O_{27}$
MW-1409.52

In another embodiment of the invention, there is provided a method of making the compound BOC-12-AD (Formula 4):

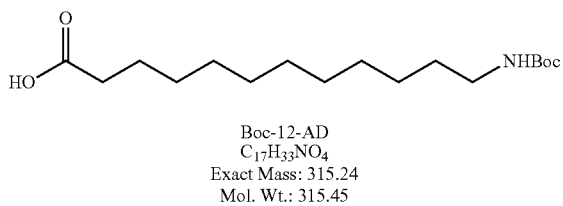 [SMILES: CC(C)(C)OC(=O)NCCCCCCCCCCCC(=O)O]

Boc-12-AD
$C_{17}H_{33}NO_4$
Exact Mass: 315.24
Mol. Wt.: 315.45 which comprises:

(i) reacting the compound 12-AD (Formula 10):

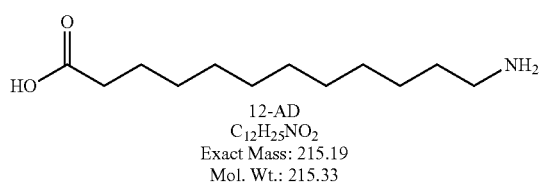 [SMILES: NCCCCCCCCCCCC(=O)O]

12-AD
$C_{12}H_{25}NO_2$
Exact Mass: 215.19
Mol. Wt.: 215.33 with methanol (MeOH) in the presence of acetyl chloride (AcCl) to yield the compound of Formula 11:

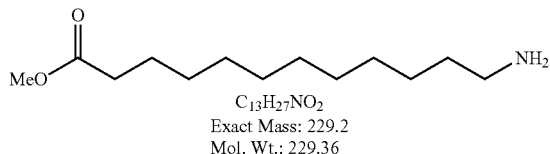 [SMILES: "C13H27NO2" ; COC(=O)CCCCCCCCCCCN]

$C_{13}H_{27}NO_2$
Exact Mass: 229.2
Mol. Wt.: 229.36 and (ii) reacting the compound of Formula 11 with di-(tert-butyl)dicarbonate ($Boc_2O$) in the presence of 4-dimethylaminopyridine (DMAP) and a tertiary amine base $R_3N$ to yield the compound of Formula 12:

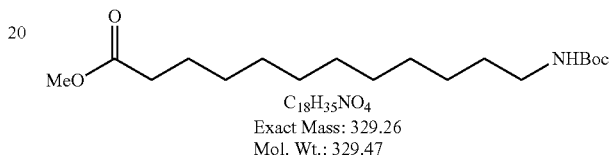

$C_{18}H_{35}NO_4$
Exact Mass: 329.26
Mol. Wt.: 329.47 wherein the tertiary amine can be but is not limited to triethylamine ($Et_3N$), diisopropylethylamine ($iPr_2NEt$), or N-methylpiperidine, and (iii) reacting the compound of Formula 12 to produce the compound of Formula 4 (Boc-12-AD).

The invention is also directed to the novel compounds of Formula 1 through Formula 12, including variations and derivatives thereof, the compounds of Formula 1 through Formula 12, including variations and derivatives thereof, produced by the methods disclosed herein, and other compounds that may be produced or generated using the methods provided herein.

The invention is directed to these and other important ends, hereinafter described.

DETAILED DESCRIPTION OF THE EMBODIMENTS

Figure 1:
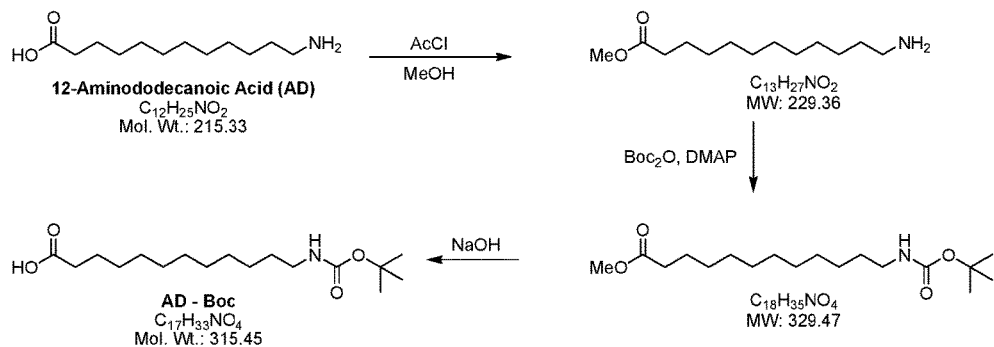
FIG. 1 shows a schematic drawing of the overall reaction to produce G-202.
Figure 1:
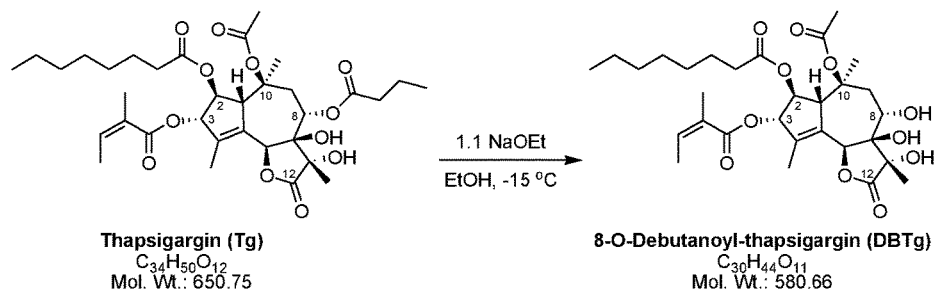
Figure 1:
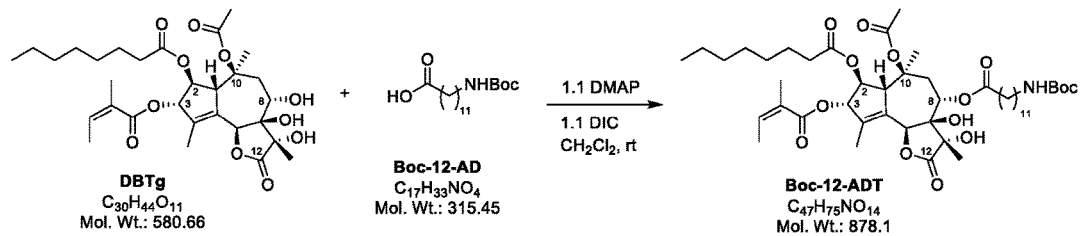
Figure 1:
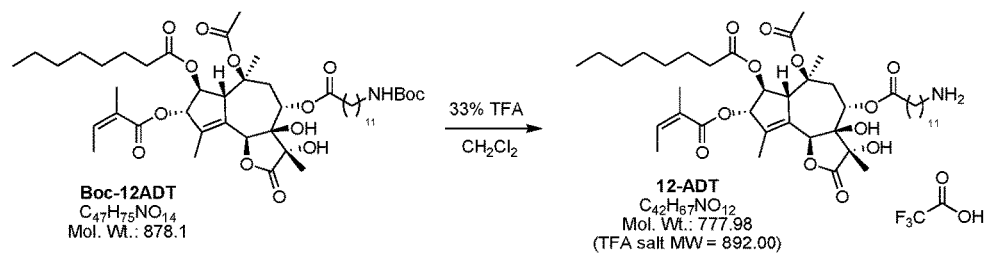
Figure 1:
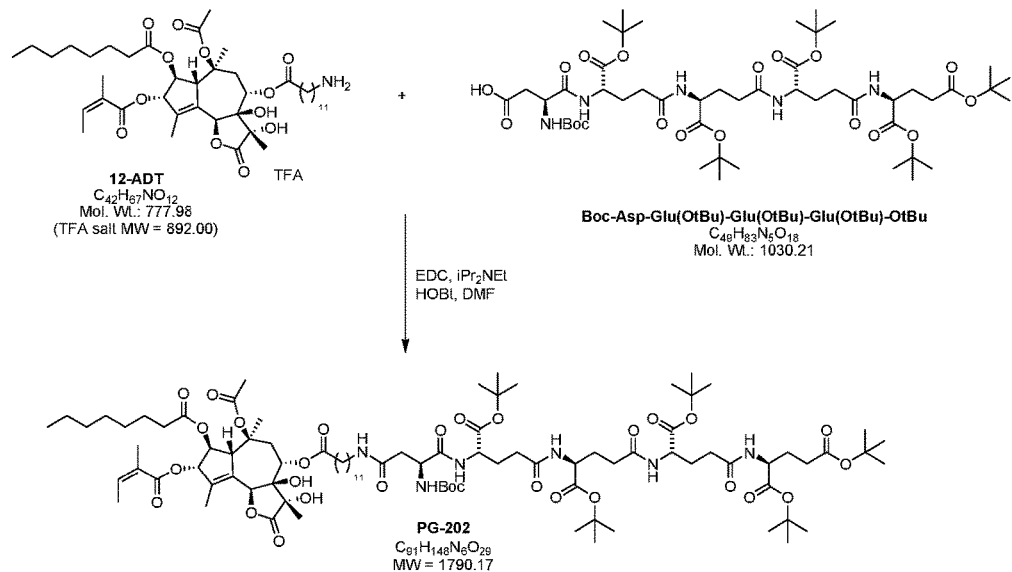
Figure 1:
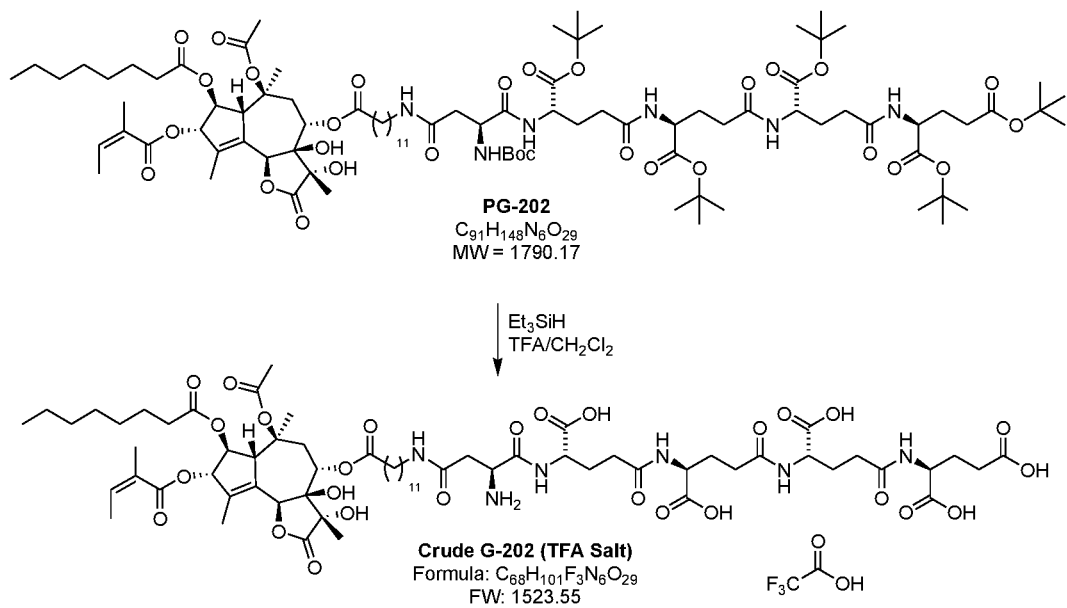
Figure 1:
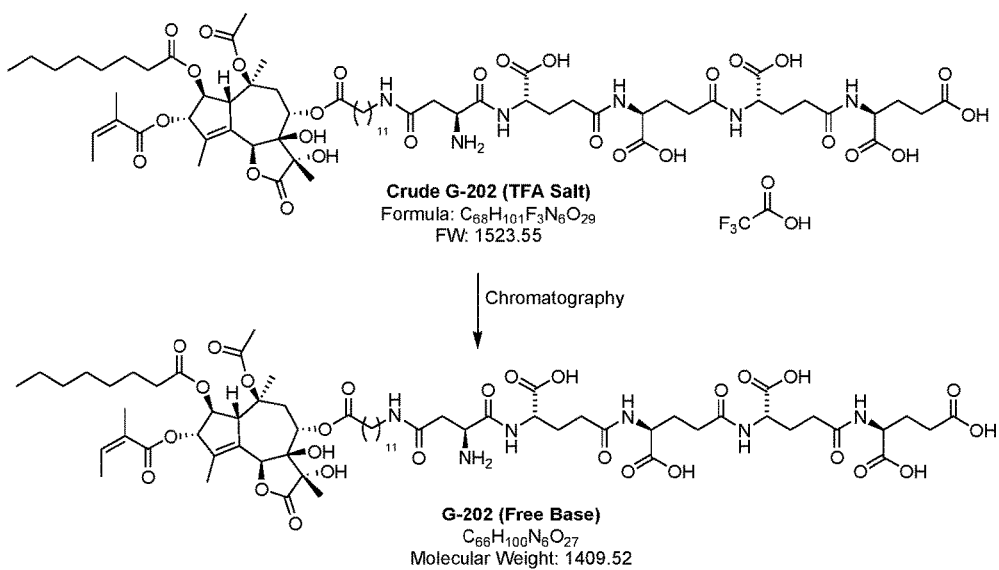

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All publications mentioned herein are cited for the purpose of describing and disclosing the cell lines, protocols, reagents and vectors which are reported in the publications and which might be used in connection with various embodiments of the invention. Nothing herein is to be construed as an admission that the invention is not entitled to antedate such disclosure by virtue of prior invention.

As used herein, the term "G-202" refers to 8-O-(12-aminododecanoyl)-8-O-debutanoyl-thapsigargin) aspartate-γ-glutamate-γ-glutamate-γ-glutamate-glutamate OH, having the chemical structure of Formula 1.

G-202 is a thapsigargin prodrug containing a cytotoxic analog of thapsigargin coupled to a masking peptide that inhibits its biologic activity until proteolytic cleavage at the tumor site. Thapsigargin itself is a natural product that is chemically modified to 8-O-(12-aminododecanoyl)-8-O-debutanoyl-thapsigargin) (12ADT). This thapsigargin analog is coupled to the beta carboxyl of Asp at the N-terminal end of the masking peptide Asp-γ-Glu-γ-Glu-γ-GluGlu to produce the prodrug (12ADT)-Asp-γ-Glu-γ-Glu-γ-Glu-GluOH (G-202).

The chemical name for G-202 is (8-O-(12-aminododecanoyl)-8-O-debutanoyl-thapsigargin) aspartate-γ-glutamate-γ-glutamate-γ-glutamate-glutamate OH. It is sometimes referred to in an abbreviated fashion: (12ADT)Asp-γ-Glu-γ-Glu-γ-Glu-GluOH, where 12ADT represents the thapsigargin derivative and Asp-γ-Glu-γ-Glu-γ-Glu-GluOH represents the PSMA-cleavable masking peptide. G-202 is a tan to white solid with a molecular weight of 1409.52.

G-202 consists of a PSMA-selective 5 amino acid peptide substrate coupled to a highly cytotoxic analog of the natural product thapsigargin. See, e.g., Denmeade, S. R., et al., *J. Natl. Cancer Inst.* 2003; 9: 990-1000; and U.S. Pat. Nos. 7,767,648 and 7,468,354. Thapsigargin is isolated from the seeds of the plant *Thapsia garganica*, which grows as a weed throughout the Mediterranean basin. See, e.g., Rasmussen, U., et al., *Acta Pharm. Suec.* 1978; 15:133-140. Thapsigargin functions by potently inhibiting a critical intracellular protein, the sarcoplasmic/endoplasmic reticulum calcium ATPase (SERCA) pump whose normal function is to maintain intracellular calcium homeostasis in all cell types. Proper function of the SERCA pump is required for the viability of all cell types. Thus, thapsigargin inhibition of the SERCA pump results in the death of all cell types tested, both normal and malignant. See, e.g., Thastrup, O., et al., *Proc. Natl. Acad. Sci. USA* 1990; 87:2466-2470; Denmeade, S. R., *Cancer Biol. Ther.* 2005; 4:14-22.

On this basis, G-202 was designed to target this potent cytotoxin with a unique mechanism of action for selective activation by PSMA produced by prostate cancer epithelial cells within sites of prostate cancer and by tumor endothelial cells in other cancer cell types, for example, hepatocellular carcinoma. Without being bound by any particular theory, it is believed that PSMA is an extracellular carboxypeptidase that sequentially cleaves off acidic amino acids from the G-202 prodrug to eventually liberate a cytotoxic analog of thapsigargin. See, e.g., Pinto, J. T., et al., *Clin. Cancer Res.* 1996; 2:1445-1451; Carter, R. F., et al., *Proc. Natl. Acad. Sci., USA* 1996; 93:749-753; Mhaka, A., et al., *Cancer Biol Ther.* 2004; 3:551-558. This highly lipophilic analog, termed 12ADT-Asp, upon release from its water soluble peptide carrier, rapidly partitions into the surrounding cell membranes. See, e.g., Jakobsen, C. M., et al., *J. Med. Chem.* 2001; 44:4696-4703. The analog then binds to the SERCA pump producing a sustained elevation in intracellular calcium which results in activation of apoptosis (see, e.g., FIG. 1; Denmeade, S. R., et al. *J. Natl. Cancer Inst.* 2003; 9: 990-1000; Singh, P., et al., *J. Med. Chem.* 48, 3005-3014 (2005)). Because the 12ADT-Asp analog is released extracellularly into the tumor microenvironment, every cell does not need to produce PSMA to be killed by the prodrug activation. A substantial bystander effect is achieved by the release of the active drug into the tumor microenvironment.

Preclinical studies with G-202 have demonstrated that the prodrug is selectively activated by PSMA in vitro and is ~60-fold more toxic to PSMA expressing vs. PSMA non-expressing tumor cells. PSMA shows significant growth inhibition against a panel of prostate, breast, renal, liver, and bladder cancers in vivo at doses that are minimally toxic to the host animal. See, e.g., Denmeade, S., et al., www-.ScienceTranslationalMedicine.org, Vol. 4, Issue 140: 1-12 (2012).

In one embodiment, the present invention provides methods for the production of G-202 (Formula 1), crude G-202 (Formula 9), and certain intermediates. The overall reaction scheme for crude G-202 is summarized and set forth as shown in FIG. 1.

Thus, in one embodiment, the compound (Formula 2)

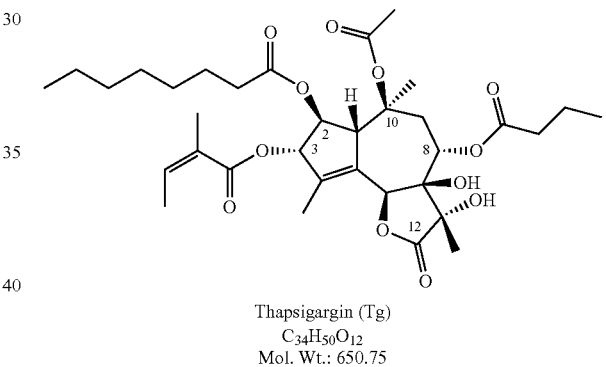

Thapsigargin (Tg)
$C_{34}H_{50}O_{12}$
Mol. Wt.: 650.75 is utilized as a starting material. This compound is reacted with sodium ethoxide in ethanol at a temperature of −15±5° C. to produce

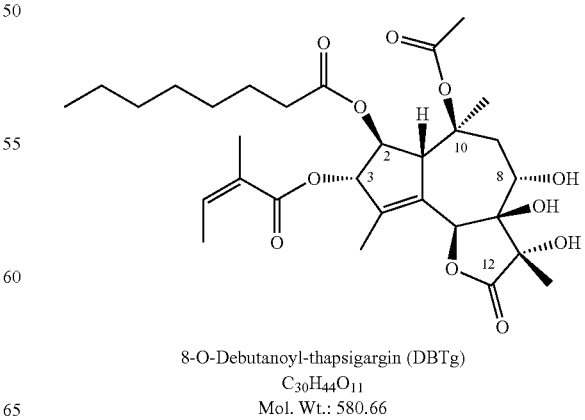

8-O-Debutanoyl-thapsigargin (DBTg)
$C_{30}H_{44}O_{11}$
Mol. Wt.: 580.66

(Formula 3). Next, this compound (8-O-debutanoylthapsigargin (DBTg)) is reacted with 4-dimethylaminopyridine (4-DMAP), 12-(tert-butoxycarbonylamino)dodecanoic acid (12-Boc-AD) and dichloromethane until a homogeneous solution is obtained. Diisopropylcarbodiimide (DIC) is added to this solution to obtain:

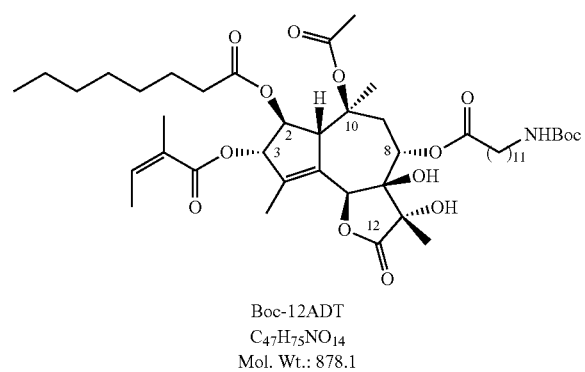

Boc-12ADT
$C_{47}H_{75}NO_{14}$
Mol. Wt.: 878.1

(Formula 5) (Boc-12ADT or 12-Boc-ADT). Boc-12ADT is dissolved in dichloromethane ($CH_2Cl_2$) and mixed with trifluoroacetic acid (TFA) to yield:

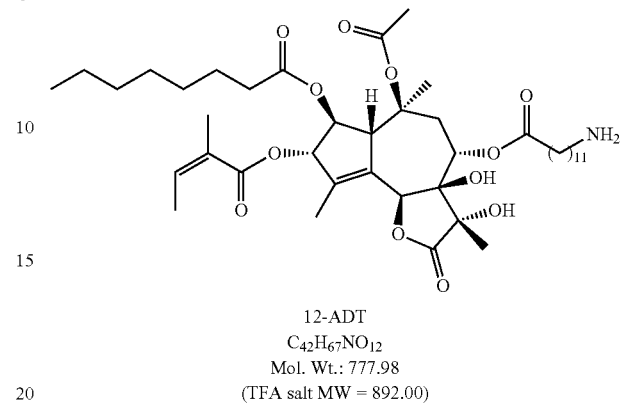

12-ADT
$C_{42}H_{67}NO_{12}$
Mol. Wt.: 777.98
(TFA salt MW = 892.00)

(Formula 6) (12-ADT). Thereafter, this compound, 12-ADT, is then reacted with the purified peptide:

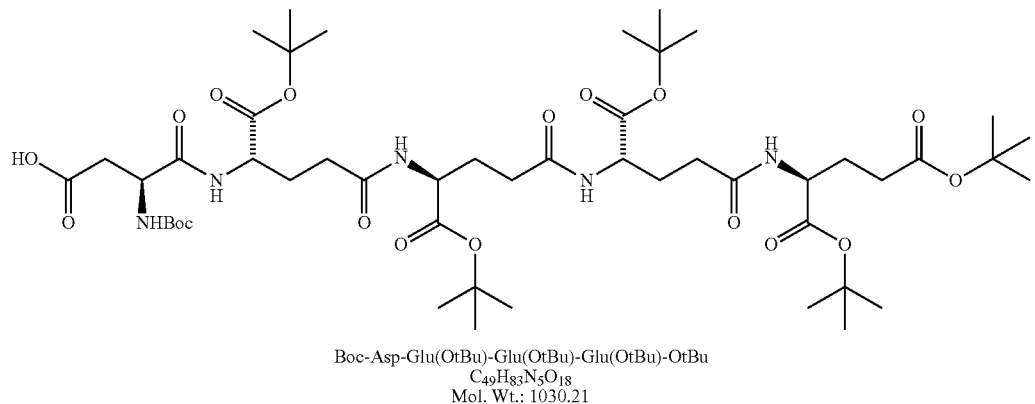 [SMILES: CC(C)(C)OC(=O)CC[C@H](NC(=O)CC[C@H](NC(=O)CC[C@H](NC(=O)CC[C@H](NC(=O)[C@H](CC(=O)O)NC(=O)OC(C)(C)C)C(=O)OC(C)(C)C)C(=O)OC(C)(C)C)C(=O)OC(C)(C)C)C(=O)OC(C)(C)C ; "Boc-Asp-Glu(OtBu)-Glu(OtBu)-Glu(OtBu)-OtBuC49H83N5O18Mol. Wt.: 1030.21"]

Boc-Asp-Glu(OtBu)-Glu(OtBu)-Glu(OtBu)-OtBu
$C_{49}H_{83}N_5O_{18}$
Mol. Wt.: 1030.21

(Formula 7) in a mixture of dimethylformamide (DMF) and hydroxybenzotriazole hydrate (HOBt). Diisopropylethylamine (DIPEA) is added to the mixture, followed by (3-Dimethylaminopropyl)ethylcarbodiimide hydrochloride (EDC-HCl) to produce:

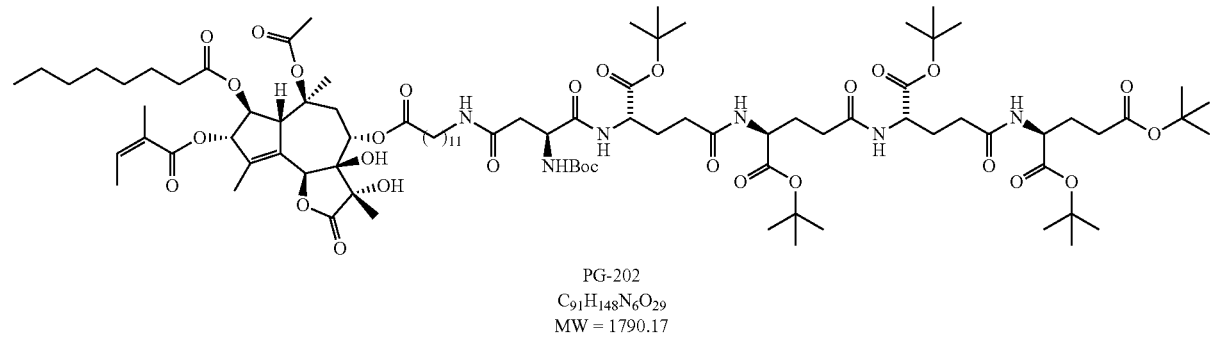

PG-202
$C_{91}H_{148}N_6O_{29}$
MW = 1790.17

(Formula 8) (PG-202). Next, this compound is reacted with dichloromethane, triethylsilane (Et₃SiH) and trifluoroacetic acid to produce the compound:

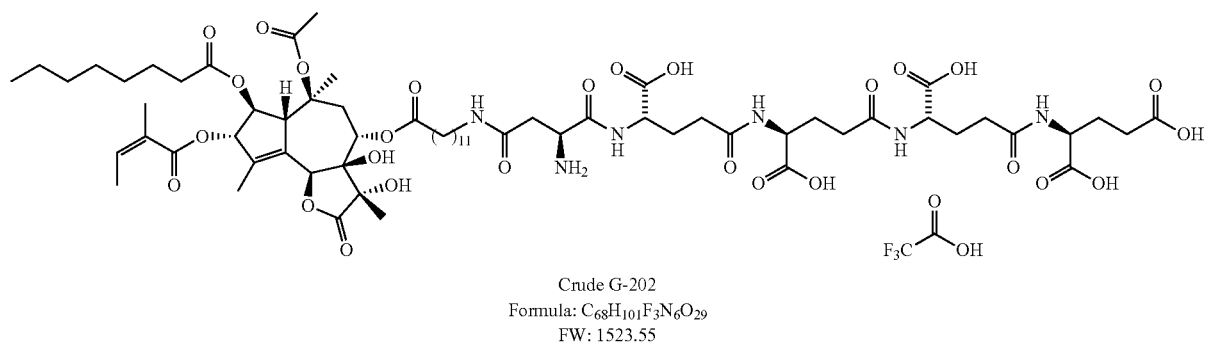

Crude G-202
Formula: $C_{68}H_{101}F_3N_6O_{29}$
FW: 1523.55

(Formula 9) (crude G-202). Crude G-202 is then purified to produce the compound of Formula 1.

The present invention also provides methods for the production of the reactant Boc-12-AD (Formula 4), which is used in the production of crude G-202 (Formula 9), as shown in the reaction scheme above. The overall reaction scheme for Boc-12-AD may be summarized and set forth as follows:

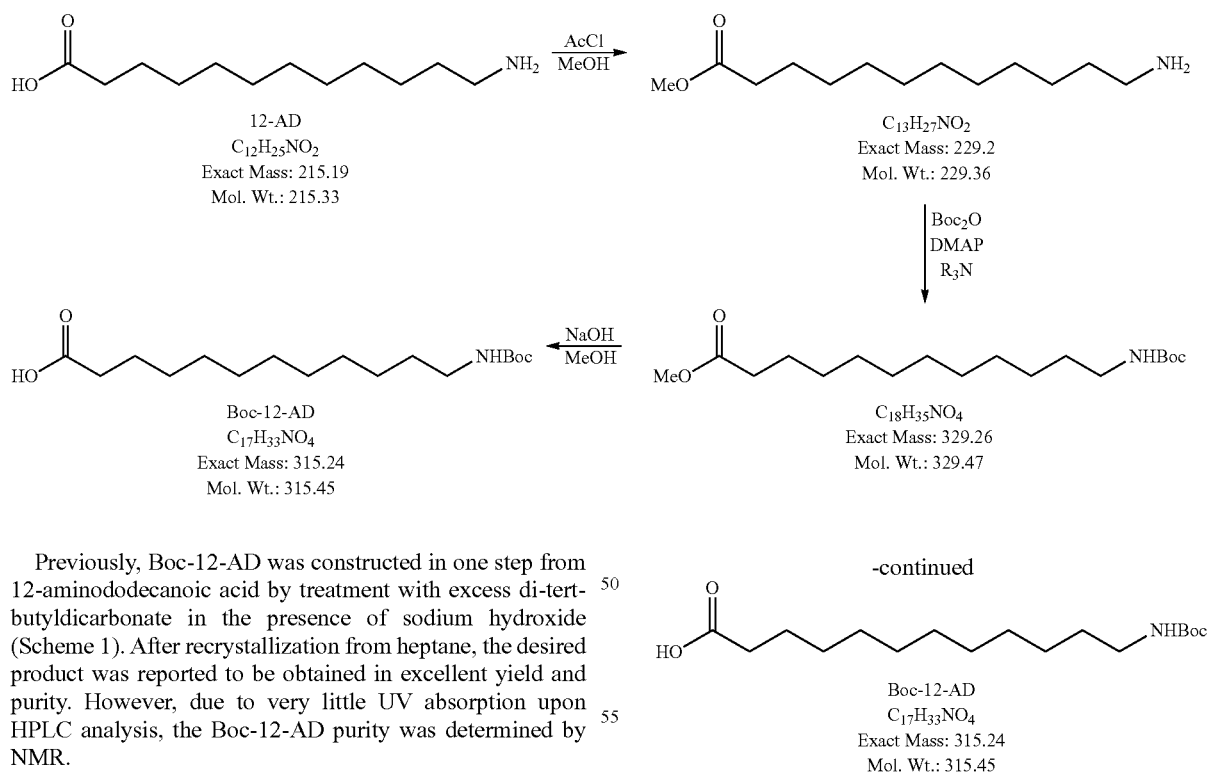

Previously, Boc-12-AD was constructed in one step from 12-aminododecanoic acid by treatment with excess di-tert-butyldicarbonate in the presence of sodium hydroxide (Scheme 1). After recrystallization from heptane, the desired product was reported to be obtained in excellent yield and purity. However, due to very little UV absorption upon HPLC analysis, the Boc-12-AD purity was determined by NMR.

Scheme 1

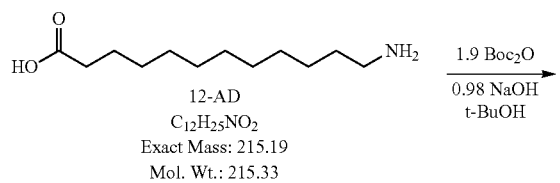

When 12-aminododecanoic acid is treated in t-butanol with 1.9 equivalents Boc₂O and 0.98 equivalents of NaOH (5 M) at 40° C., followed by a workup and recrystallization from heptane, it is expected to produce pure Boc-12-AD. However, while the material produced by this method is snow-white and crystalline, analysis by 1 c/ms indicated that it contained significant amounts of three compounds as shown below (Scheme 2). Due to significant signal overlap, it is likely these impurities are not identifiable by NMR.

Scheme 2

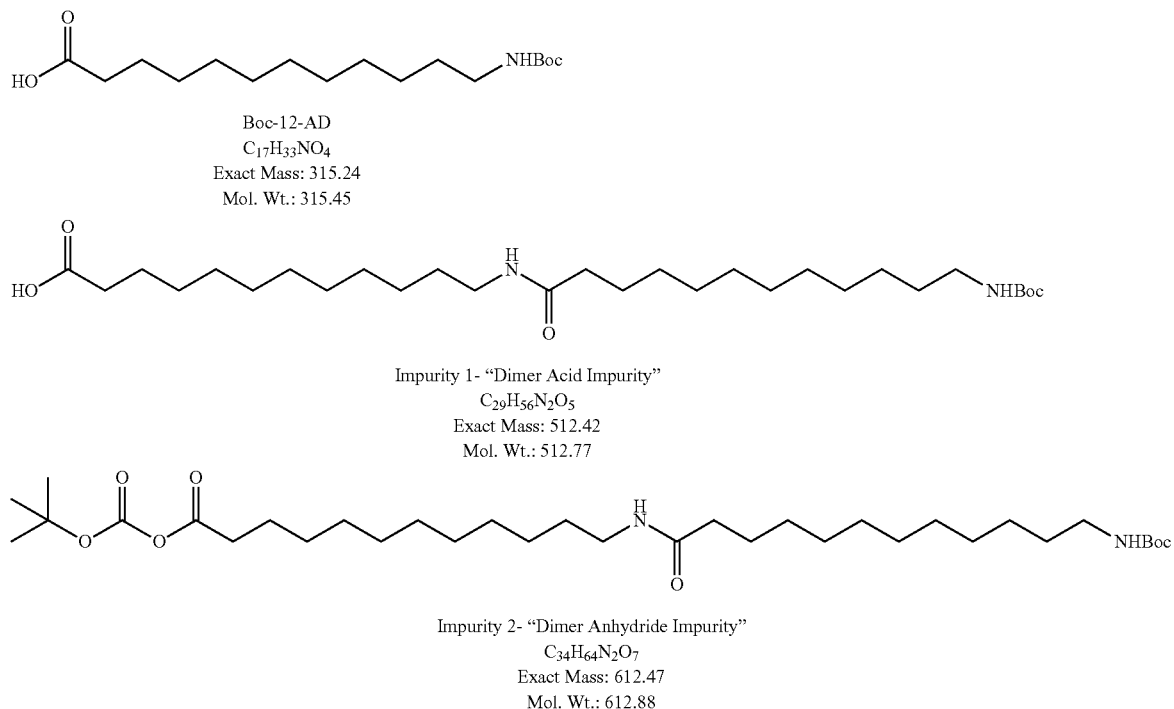

Thus, one of the components produced by Scheme 1 is the required Boc-12-AD, but the two others are dimers of the starting material. From structural assignments based solely on 1 c/ms, impurity 1 is believed to be the free acid and impurity 2 is believed to be the t-butyl anhydride. Analysis of the material before and after the first recrystallization from heptane indicated that it was not effective at removing these impurities. A second crystallization from heptane was found to reduce the amount of impurity 2, but did not reduce impurity 1. The material can also be recrystallized from ethyl acetate or a mixture of methyl t-butyl ether (MTBE) and heptane with good recovery. However, both systems reduce impurity 2 but have little effect on the amount of impurity 1. If left in the reactant, impurity 1 will react with DBTg and create impurities throughout the rest of the synthesis which are very difficult to remove.

Thus, provided herein is a novel method that essentially eliminates the impurities generated in the existing synthesis. The method includes the generation of Boc-12-AD via the three-step route shown in Scheme 3 below.

Scheme 3

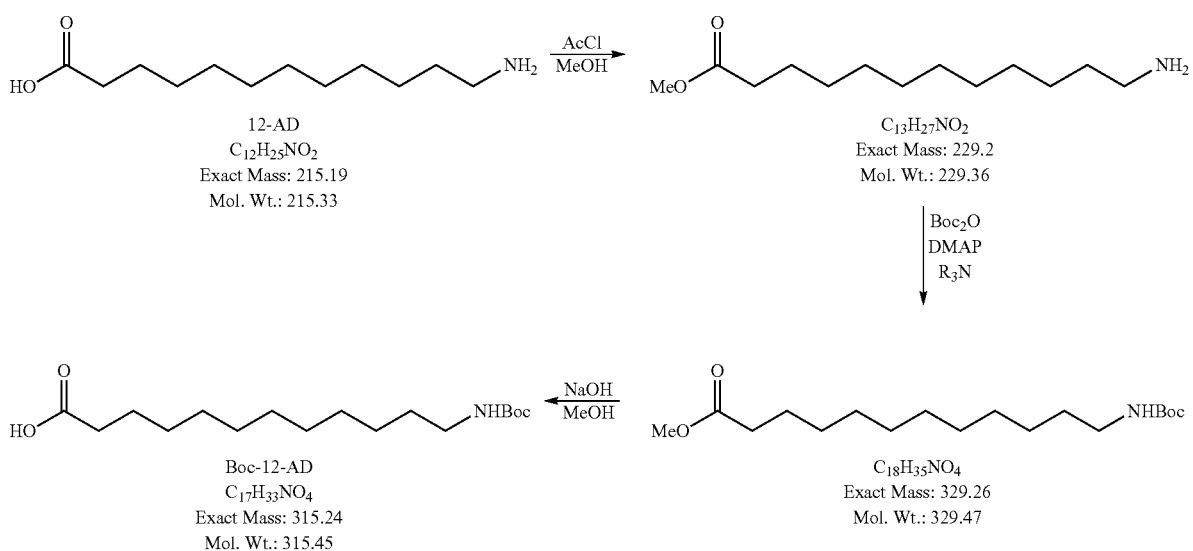

Acid-catalyzed esterification of 12-aminododecanoic acid generates the methyl ester hydrochloride. This reaction was followed by protection of nitrogen as the t-butyl carbamate and finally hydrolysis to give the desired product.

While this route is longer (3 steps versus 1), it is very high-yielding (96%, 97% and 98% for each step respectively) and it essentially eliminates the formation of the dimer impurities. Additionally, for the reaction to convert DBTg to Boc-12-ADT, the byproduct diisopropylurea (DIU) is removed by precipitation from MTBE/heptane; unreacted DIC is removed by a novel ACN/heptane partitioning, and a silica gel purification of 12-ADT-TFA was developed.

Scheme 3 may also be used to generate variations of Boc-12-AD, for example, compounds having the formula Boc-$(CH_2)_n$—$NH_2$, wherein n is an integer greater than 2. For such compounds, the starting material will have the formula $(CH_2)_n$—$NH_2$, wherein n is an integer greater than 2 (Formula 13).

In another embodiment, the present invention provides the compounds of Formula 1 through Formula 12, including variations and derivatives thereof, and methods of using the same. In another embodiment, the present invention provides the compounds of Formula 1 through Formula 12, including variations and derivatives thereof, made by the methods disclosed herein.

EXAMPLES

The invention will now be described in greater detail by reference to the following non-limiting examples.

Example 1: Preparation of 8-O-Debutanoylthapsigargin (DBTg)

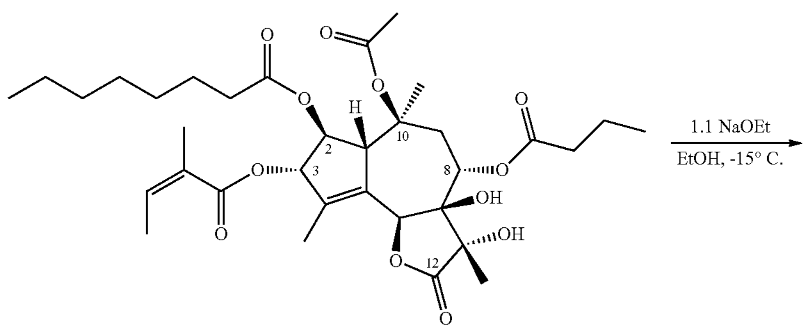

Thapsigargin (Tg)
$C_{34}H_{50}O_{12}$
Mol. Wt.: 650.75

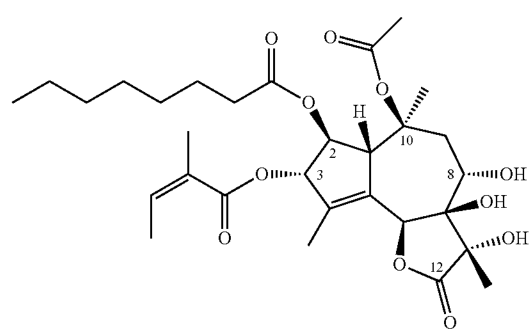

8-O-Debutanoyl-thapsigargin (DBTg)
$C_{30}H_{44}O_{11}$
Mol. Wt.: 580.66

A 22-L round bottom flask (RBF) was charged with 709 g of thapsigargin (weight corrected for water and solvents was 693 g) followed by 4.6 L of ethanol. The mechanical stirrer was started; the material stirred until homogeneous, and then cooled to −15±5° C. with a 75/25 methanol/water/dry ice bath. A 20% solution of sodium ethoxide in ethanol (445 ml) was added slowly while keeping the temperature −15±5° C. An in-process reaction check at 20 minutes indicated complete reaction (1% Tg) and glacial acetic acid (85 ml) was added quickly to quench the reaction. After the quench, the reaction was allowed to warm and concentrated on a rotovap to remove the bulk of the ethanol. The resultant thick oil was dissolved in methyl t-butyl ether (MTBE) and washed with deionized water, saturated sodium bicarbonate, deionized water, and saturated sodium chloride. The organic layer was dried over sodium sulfate, filtered and concentrated on a rotovap. After co-distilling with MTBE (2×) the resultant amorphous dry foam/solid was placed in a vacuum oven and dried without heat for 15 hours and 56 minutes. The weight of DBTg was 613 grams (95% recovery) with 97% purity by HPLC area and no ethanol detected. The material passed all specifications and was released.

Example 2: Preparation of 12-ADT-TFA

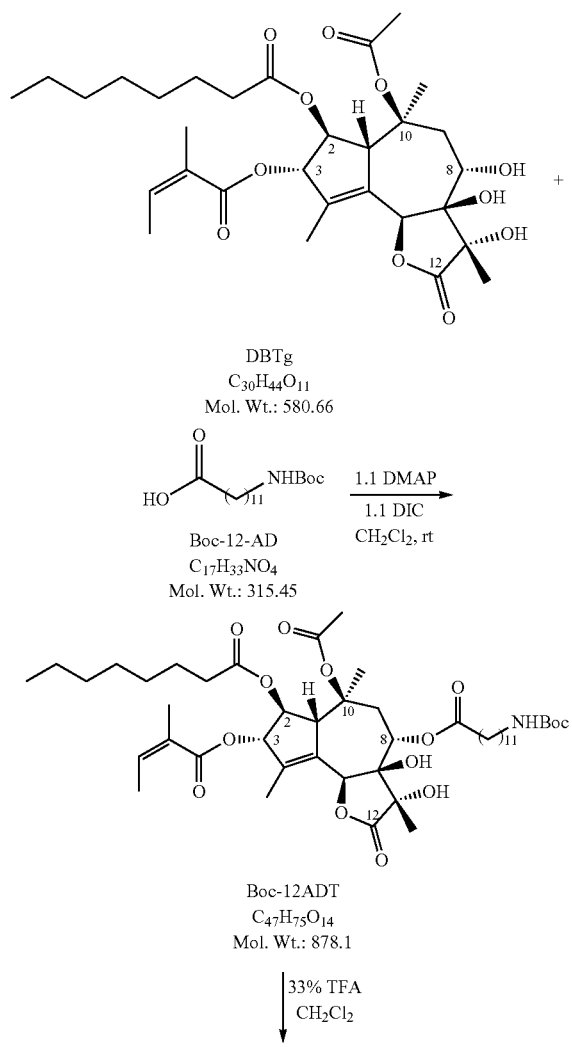

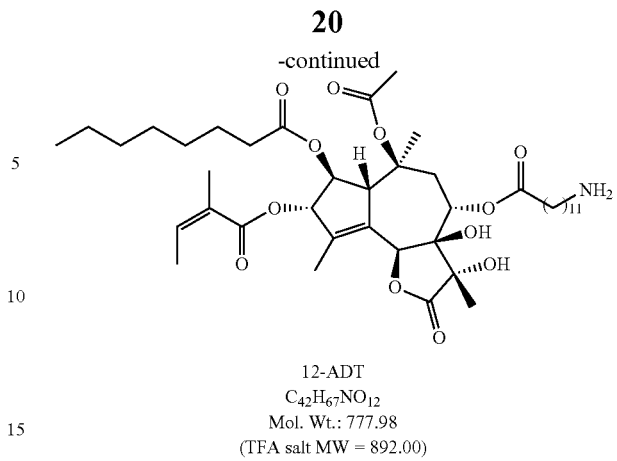

12-ADT
$C_{42}H_{67}NO_{12}$
Mol. Wt.: 777.98
(TFA salt MW = 892.00)

A 12-liter round bottom flask was charged with 607 grams of 8-O-debutanoylthapsigargin (DBTg), 139 grams of 4-dimethylaminopyridine (4-DMAP), 342 grams of 12-(tert-butoxycarbonylamino)dodecanoic acid (12-Boc-AD) and 2050 ml of dichloromethane. The contents of the flask were stirred until a homogeneous solution was obtained followed by addition of the diisopropylcarbodiimide (DIC, 192 ml). After passing a reaction check at 3 hours, the dichloromethane was removed by concentration on a rotovap followed by chasing with MTBE. The reagent byproduct diisopropylurea (DIU) was removed by precipitation from MTBE and heptane followed by filtration. The organic mother liquor was transferred to a separatory funnel and the material washed with 0.5 M HCl (2×), 0.6 M sodium bicarbonate (2×), and saturated sodium chloride. The organic layer was dried over sodium sulfate, filtered and concentrated. In order to remove residual reagent DIC, the material was dissolved in acetonitrile (CAN) and washed with n-heptane. The CAN layer was transferred to the rotovap, concentrated, and then co-distilled with MTBE to remove CAN. The resultant 12-Boc-ADT was dissolved in dichloromethane, transferred to a 22-L round bottom flask and cooled to <10° C. Trifluoroacetic acid was added via addition funnel while maintaining a temperature <15° C. An in-process reaction check at 30 minutes indicated no starting material remained. The reaction solution was transferred to a rotovap, concentrated and co-distilled with dichloromethane (2×). The material was further purified by plug filtration through silica gel. The material was loaded onto the silica bed with dichloromethane and eluted with dichloromethane (4 column volumes CVs), 10% acetone/90% dichloromethane (8 CVs) and then acetone (20 CVs) to give 658 grams of 12-ADT-TFA (71% yield for two steps) with a purity of 98% by area, 0.12% dichloromethane and 1.6% acetone.

Example 3: Preparation of PG-202

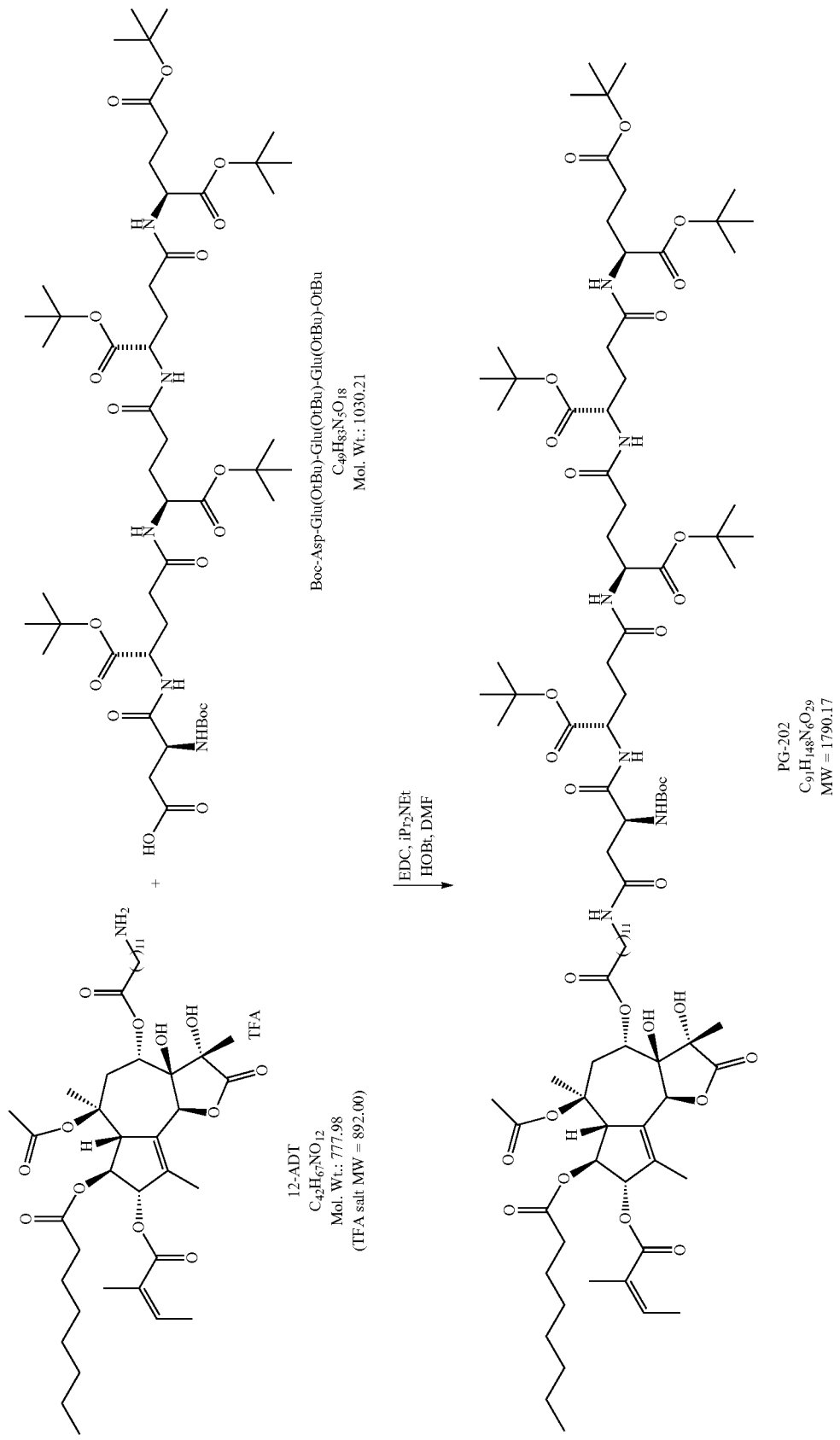

Residual ammonium acetate was removed from the peptide (774 g) by dissolving the peptide in MTBE and washing with 0.5 M HCl, deionized water, and saturated sodium chloride. The resultant organic solution was dried over sodium sulfate, filtered and concentrated. This was followed by dissolving in MTBE and azeotropic distillation with heptane. The purified peptide was charged to a 12-L RBF followed by DMF (1.3 L), hydroxybenzotriazole hydrate (242 g), 12-ADT-TFA (644 g), and an additional 1.8 L of DMF. Next, DIPEA (153 ml) was added followed by EDC-HCl. The first reaction check at 6 hours and 5 minutes indicated significant starting material remained (22.6% 12-ADT-TFA). The second reaction check at 12 hours and 24 minutes indicated the reaction had stalled (22% 12-ADT-TFA). Therefore, after 13 hours and 6 minutes additional EDC-HCl was added (48 g, 0.35 equiv). The reaction was allowed to stir overnight and an in-process check at 24 hours 40 minutes indicated the reaction had progressed but 18% 12-ADT-TFA still remained. At 25 hours and 16 minutes, additional DIPEA was added (153 ml, 1.22 equiv). The next reaction check (26 hrs 17 minutes) showed 10% remaining 12-ADT-TFA. This indicated that additional base was driving the reaction forward. Another DIPEA charge (158 ml, 1.26 equiv) at 28 hrs 15 minutes pushed the reaction to 95% completion (30 hours 20 minutes). The reaction mixture was diluted into MTBE, washed with 0.5 M HCl (2×), deionized water (2×), saturated sodium bicarbonate, and saturated sodium chloride. The organic layer was dried over sodium sulfate, filtered and concentrated. The PG-202 was dissolved in dichloromethane, placed on 10 kg of silica, and eluted with six column volumes of 55% n-heptane:45% acetone. The eluent was concentrated on a rotovap, and azeotroped with MTBE to give 1048.7 grams of PG-202 (72% yield) as an off-white powder that passed all specifications. The purity was 89% and the material contained 2.9% MTBE, 0.76% n-heptane, and 0.049% DMF.

Example 4: Preparation of Crude G-202

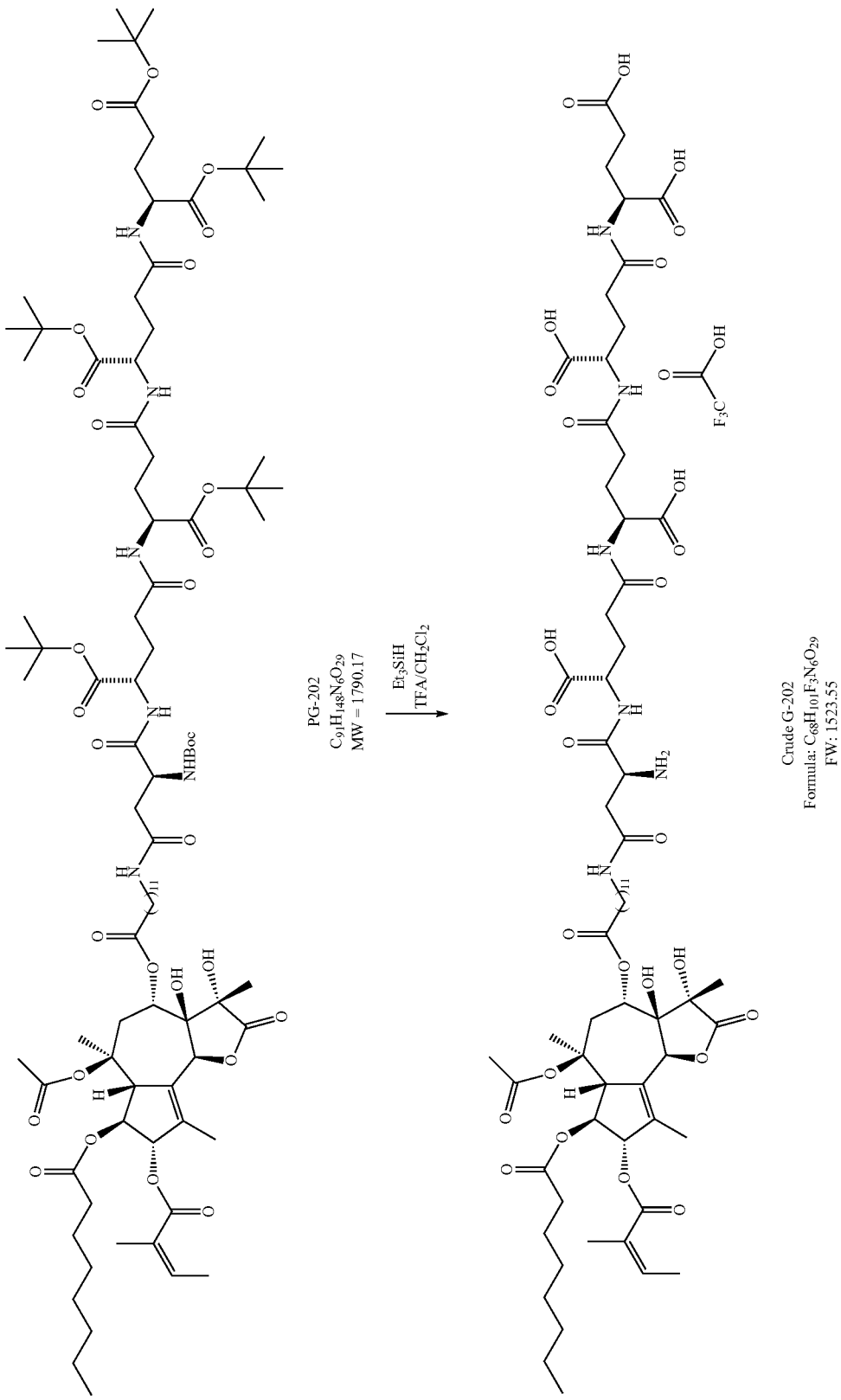

A 22-L round bottom flask was charged with PG-202 (500 grams), 2.8 liters of dichloromethane and 360 ml of triethylsilane. The material was stirred until homogeneous and then cooled to ≤10° C. Trifluoroacetic acid (2.8 L) was added while maintaining temperature ≤10° C. (31 minutes). The reaction was stirred at ≤10° C. for 34 minutes and then the cooling bath was removed and the reaction allowed to warm to room temperature. A reaction check after 16 hours and 52 minutes indicated the reaction was complete. The reaction mixture was transferred to a rotary evaporator and concentrated to an oil. This was followed by co-distillation with DCM (4×5.5 L) to obtain a solid that was dried in a vacuum oven at ≤40° C. for 12 hours and 6 minutes to give 513 grams of crude G-202 (68.5% yield) as an off-white powder. The purity was 79% by HPLC area % and 50.5 weight %. The material passed all specifications and was released.

The crude G-202 was purified by C18 reverse-phase chromatography followed by a concentration column which reduced the volume of water before lyophilization and converted the TFA salt into the free base. The G-202 was purified in several runs, one example of which is described below.

Example 5: Reverse-Phase Chromatographic Purification Biotage 150 L KP-C18-HS Column-Run 1

The load for the first run was the crude G-202 (HCN 5541-08411-A) which was dissolved in 2.64 L of 50% ACN/WFI with 0.1% TFA, diluted with WFI to 35%, and stored at ambient temperature overnight. The load solution was filtered through a sintered glass filter (4-5.5 μm) and loaded onto the column. The column was eluted with 35%, then 40%, followed by 45% acetonitrile/WFI with 0.1% TFA. The elution was monitored by UV at 235 nm. As expected, G-202 eluted off in 45% acetonitrile/WFI with 0.1% TFA. When G-202 came off the column, one gallon fractions were collected and assayed by the short HPLC method (P/N 5300.000). Based on HPLC chromatographic purity, the fractions with area %>95% were combined to make two mini-pools (45% F3-F18 and 45% F4-F17) which were analyzed by HPLC (P/N 5289). Both mini-pools showed >98% chromatographic purity. Therefore, 45% F3-F18 were combined to give a G-202 product pool (54 L) containing 95.7 g G-202 as determined by HPLC using the G-202 TFA salt (2695-64-15) as standard.

Example 6: Concentration-Purification Column Run 1

The G-202 product pool (54 L) from run 1 was diluted with the given volume of water to make a 25% can/WFI solution, and reloaded on the Biotage 150M KP-C4-WP column which had been equilibrated with 25% ACN/WFI (20 L). The column was rinsed with 25% ACN/WFI to remove TFA, and 40% ACN/WFI to remove the impurity with RRT 0.65. At the end of 40% ACN/WFI elution, G-202 started to come off. The C4-WP column was continued eluting with 90% ACN/WFI. G-202 was concentrated in about 4 L of 40% ACN/WFI and 15 L of 90% ACN/WFI.

Example 7: Synthesis of the t-Butylcarmate Protected Linker (BOC-12-AD) (Formula 4)

BOC-12-AD was synthesized according to the scheme below:

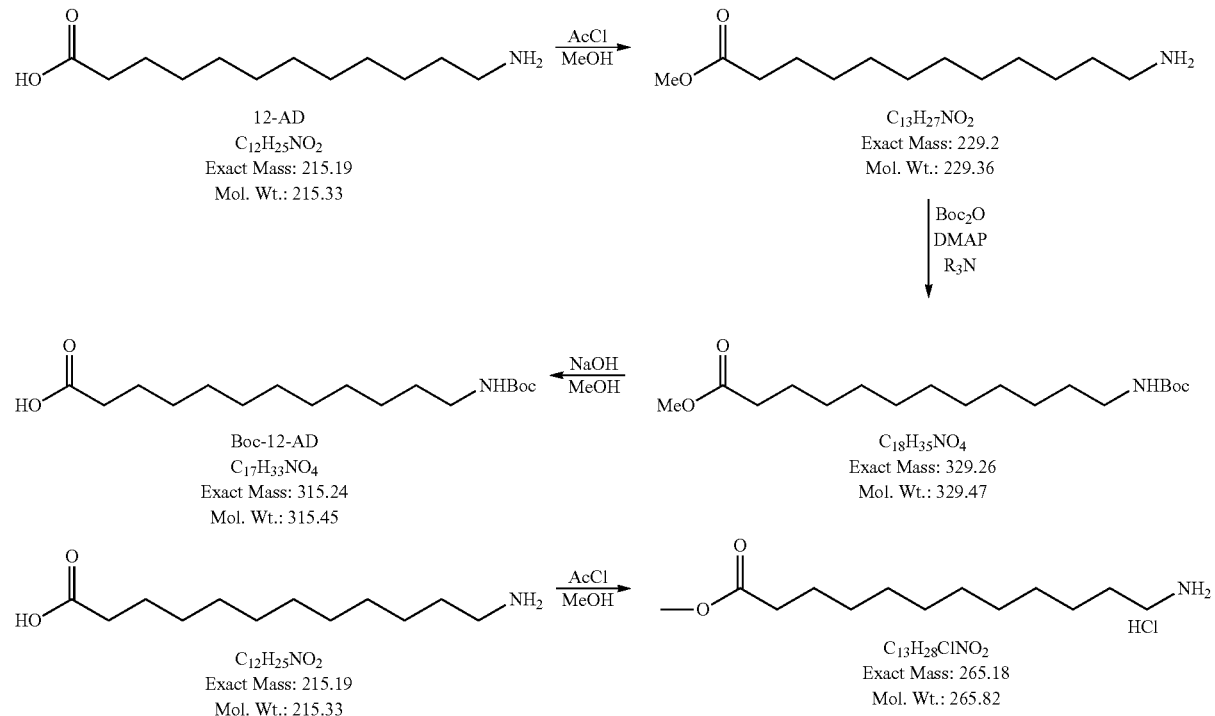

A 22 L 3N RBF was flushed with $N_2$ and placed under a $N_2$ bleed. The flask was charged with 14 L of MeOH followed by 825 mL (2.5 eq.) of acetyl chloride which was added via addition funnel over ca. 45 minutes. There is an exotherm of ca. 10° C. during the addition. The resulting solution was cooled to <25° C. and 1.0 Kg (1.0 eq.) of (1, as shown in the scheme above) is added all at once at room temperature. The reaction mixture was stirred for ca. 1.5 hr. at room temperature and considered complete based on LC/MS. The reaction mixture was concentrated to a total volume of ca. 4.5 L removing the majority of the MeOH to form a thick white slurry. To the slurry at room temperature 5.5 L of MTBE was added and the resulting suspension cooled to <10° C. for ca. 1 hr. The product was isolated via filtration and washed 3 times with ca. 3 L of cold MTBE. The product (2, as shown in the scheme above) was dried a short time on the filter transferred to a drying tray and further dried overnight in the vacuum oven at ca. 45° C. to give 1197 g of (2) as a white crystalline solid (97%) recovery.

A 22 L 3N RBF was flushed with $N_2$ and placed under a $N_2$ bleed. The flask was charged with 525 g (1.0 eq.) of (2), 6.0 L of $CH_2Cl_2$, 24.1 g (0.1 eq.) of DMAP and 451 g (1.05 eq.) of $Boc_2O$. The above materials were rinsed forward with 2.0 L of additional $CH_2Cl_2$. Next, 577 mL (2.1 eq.) of triethylamine was added drop wise over 20-25 min. via addition funnel. There was a slight exotherm and moderate gas evolution during the addition. A light amber solution forms during the addition. The reaction mixture was stirred for ca. 1 hr. at room temperature and determined complete TLC. The reaction mixture was diluted with 3.0 L of $CH_2Cl_2$ and 3.0 L of 1M HCl added before stirring for ca. 10 minutes. Layers were separated and the organics washed 1×3.0 L of sat. $NaHCO_3$. The organics were dried over $Na_2SO_4$, filtered and concentrated to ca. 1.0 to 1.4 L total volume a very light suspension formed. The drying salts were washed 3 times with a total of 1.0 L of MTBE. The MTBE was removed via concentration on the rotovap back down to a total volume of ca. 1.0 L to remove residual $CH_2Cl_2$. The light suspension that formed was diluted with 1.5 L of additional MTBE and stirred overnight. The insoluble urea impurity was removed via filtration and the solids washed three times with a small amount of MTBE. The filtrate containing the product was combined with the filtrate from a second run (same scale) and the combined filtrates were concentrated to a volume of ca. 1-1.4 L resulting in a thick light green clear oil. The oil was cooled to room temperature with stirring. During the cooling process the product began to crystallize.

To the stirring suspension 3.0 L of heptane was added at room temperature and the suspension further cooled to <10° C. The suspension was held for ca. 1.5 hr. at <10° C. before isolation via filtration. The product (3) was washed 3× with a total of 2.0 L cold heptane dried a short time on the funnel and transferred to drying trays. The product was dried under full vacuum at room temperature over night to give 1247 g of (3) as a white crystalline solid (96%) recovery.

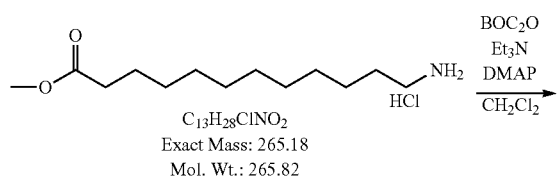

$C_{13}H_{28}ClNO_2$
Exact Mass: 265.18
Mol. Wt.: 265.82

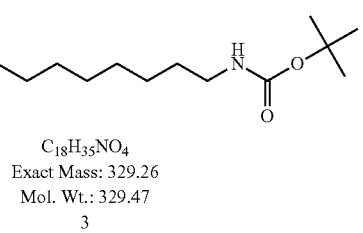

$C_{18}H_{35}NO_4$
Exact Mass: 329.26
Mol. Wt.: 329.47

3

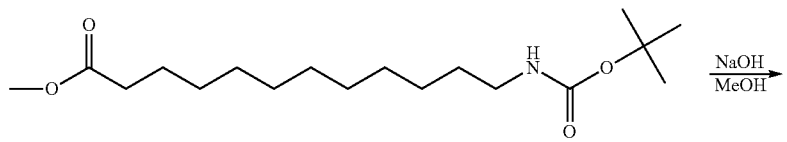

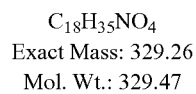

$C_{18}H_{35}NO_4$
Exact Mass: 329.26
Mol. Wt.: 329.47

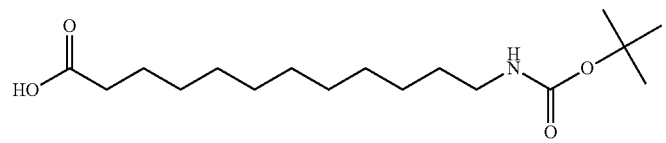

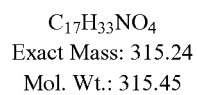

$C_{17}H_{33}NO_4$
Exact Mass: 315.24
Mol. Wt.: 315.45

4

A 22 L 3N RBF was flushed with $N_2$ and placed under a $N_2$ bleed. The flask was charged with 5.3 L of MeOH and the stirrer started. Next, 550 g (1.0 eq.) of (3) was added and rinsed with an additional 2.0 L of MeOH. To the stirring solution 4.17 L of 1M NaOH (2.5 eq.) via addition funnel over ca. 30-40 minutes. The resulting slurry was heated to ca. 50° C. and complete by TLC after 30 minutes. During the heating a solution is formed. The solution was cooled to <30° C. and quenched with 1.0 L of 6 M HCl over 30 minutes (pH~3) a white slurry develops. The slurry was stirred at room temperature for ca. 1 hr and the product (4) isolated via filtration. The product was rinsed out of the flask with ca 1.0 to 1.5 L of DI water, the product was washed with 1.0 L of water in two portions dried a short time on the filter and transferred to a tared drying trays. The product was further dried over weekend ca. 40° C. under full vacuum to give 508.5 g of (4) as a white solid (97%) recovery. The second batch (same scale) was done the same as batch 1 and produced 513.7 g of (4) a yield of 98%.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps of the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Other embodiments are set forth within the following claims.

What is claimed is:

1. A method of producing the compound of Formula 14

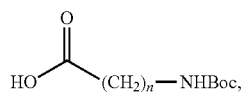

where n is an integer greater than 2, the method comprising esterify, by acid catalysis with acetyl chloride in methanol, the compound of Formula 15

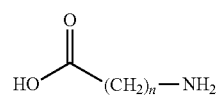

to form the compound of Formula 16

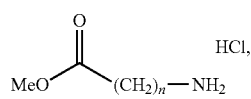

react the compound of Formula 16 with $Boc_2O$ to form the compound of Formula 17

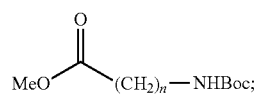

and
hydrolyze the compound of Formula 17 with NaOH to form the compound of Formula 14.

2. The method of claim 1, wherein the compound of Formula 14 is Boc-12-AD (4)

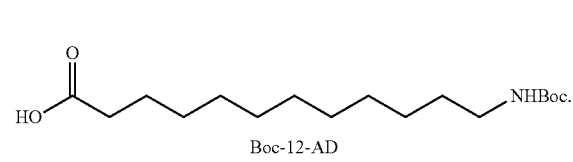

3. The method of claim 1, wherein the reaction with Boc$_2$O with the compound of Formula 16 is in CH$_2$Cl$_2$ in the presence of dimethylaminopyridine and a tertiary amine base.

4. The method of claim 3, wherein the tertiary amine base is triethylamine.

5. The method of claim 1, wherein the yield of the compound of Formula 14 is at least 97%.

6. A method of producing Boc-12-AD, having Formula 4

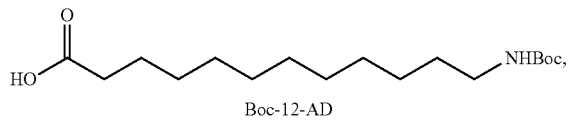

Boc-12-AD the method comprising esterify, by acid catalysis with acetyl chloride in methanol, 12-AD, having Formula 10

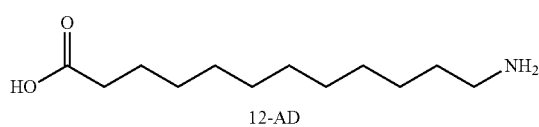

12-AD to form the compound of Formula 11

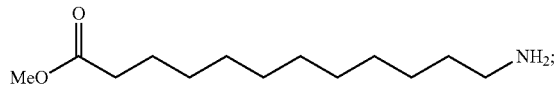

react the compound of formula 11 with Boc$_2$O to form the compound of Formula 12

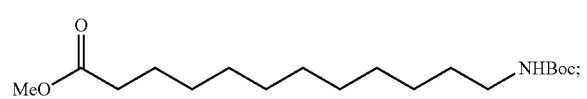

and
hydrolyze the compound of Formula 12 with NaOH to form the compound of Formula 4.

7. The method of claim 6, wherein the reaction with Boc$_2$O with the compound of Formula 11 is in CH$_2$Cl$_2$ in the presence of dimethylaminopyridine and triethylamine.

8. The method of claim 1, wherein the compound of Formula 14 comprises essentially no dimer impurities.

9. The preparation of claim 8, wherein the compound is Boc-12-AD, having Formula 4.

* * * * *